United States Patent [19]
Jacobson et al.

[11] Patent Number: 4,612,315
[45] Date of Patent: Sep. 16, 1986

[54] BIOLOGICALLY-ACTIVE 1,3-DIPROPYL-8-PHENYLXANTHINE DERIVATIVES

[75] Inventors: Kenneth A. Jacobson, Silver Spring, Md.; John W. Daly, Washington, D.C.; Kenneth L. Kirk, Bethesda, Md.

[73] Assignee: The United States of America as represented by the Department of Health and Human Services, Washington, D.C.

[21] Appl. No.: 664,953

[22] Filed: Oct. 26, 1984

[51] Int. Cl.[4] .................... A61K 31/41; C07D 473/06
[52] U.S. Cl. .................... 514/263; 514/265; 544/269; 544/271; 544/273
[58] Field of Search ............... 514/263, 265; 544/271, 544/269, 273

[56] References Cited
U.S. PATENT DOCUMENTS
4,397,779 8/1983 Groman ..................... 260/112.5 R FOREIGN PATENT DOCUMENTS
92398 10/1983 European Pat. Off. ............ 544/267

OTHER PUBLICATIONS
Bruns, Proc. Natl. Acad. Sci., USA, 80, pp. 2077–2080, (4/83).

Primary Examiner—Donald G. Daus
Assistant Examiner—Robert Benson
Attorney, Agent, or Firm—John S. Roberts, Jr.

[57] ABSTRACT

Certain functionalized congeners of 1,3-dialkylxanthine exhibit high potency and selectivity as antagonists for $A_1$- and $A_2$-adenosine receptors and are suitable for attachment to probes, drug carriers, or solid supports. These derivatives are characterized by the presence of a phenyl at the 8 position para-substituted with a functionalized chain to provide high water solubility and high receptor affinity to such an extent that these compounds are suitable for use as antiallergenic, antiasthmatic, or cardiotonic drugs, central nervous system stimulants, and diuretics.

8 Claims, No Drawings

BIOLOGICALLY-ACTIVE 1,3-DIPROPYL-8-PHENYLXANTHINE DERIVATIVES

BACKGROUND

Certain functionalized congeners of 1,3-dialkylxanthine exhibit high potency and selectivity as antagonists for $A_1$- and $A_2$-adenosine receptors and are suitable for attachment to probes, drug carriers, or solid supports. These derivatives are characterized by the presence of a phenyl at the 8 position para-substituted with a functionalized chain to provide high water solubility and high receptor affinity to such an extent that these compounds are suitable for use as antiallergenic, antiasthmatic, or cardiotonic drugs, central nervous system stimulants, and diuretics.

Alkylxanthines, of which theophylline is the most well known, represent a major class of antagonists for adenosine receptors. Although theophylline and other xanthines such as caffeine are relatively weak adenosine antagonists, with affinity constants in the 10-50 micromolar range, they owe many of their pharmacological effects to blockage of adenosine mediated functions at the $A_1$ and $A_2$ receptor sites noted above. The $A_1$-adenosine receptor is inhibitory to adenylate cyclase and appears involved in antilipolytic, cardiac, and central depressant effects of adenosine. The $A_2$-adenosine receptor is stimulatory to adenylate cyclase and is involved in hypotensive, antithrombotic, and endocrine effects of adenosine. Some xanthines, such as 3-isobutyl-1-methylxanthine, not only block adenosine receptors but also have potent inhibitory effects on phosphodiesterases. In an effort to identify highly potent and specific analogs of adenosine receptor antagonists (xanthines) the functionalized "congener approach" was applied, as described in Jacobson et al, *J. Med. Chem.*, 1983, Vol. 26, p. 492. Analogs of adenosine receptor ligands bearing functionalized chains are synthesized and covalently attached to various organic moieties, such as amines and peptides. The binding affinities (competitive CHA binding on rat cerebral cortex) and the specificity are modulated by changes in the attached moiety. The present invention discloses that the presence of a functionalized chain linked to the 8-phenyl group through a —O—CH$_2$CO— linkage greatly enhances the potency of 1,3-dialkylxanthines as adenosine antagonists. Potent antagonists are produced by replacing the 1,3-methyl groups of 8-phenyltheophylline with n-propyl groups and by situating uncharged electron-donating para-substituents on the 8-phenyl ring. In addition to high potency, some of these 1,3-dipropyl-8-phenylxanthine derivatives exhibit selectivity toward either the $A_1$- or $A_2$-subclass of adenosine receptors.

Many of the xanthines (such as theophyline) exhibit undesirable side-effects, such as caroiac stimulation. The present invention avoids or reduces these side-effects by developing compounds that are more potent or selective adenosine receptor blockers.

In the design of active covalent conjugates of drugs, the goals of the congener approach are several, including increasing the potency, prolonging the duration of action, and/or changing the specificity. As noted above, they are useful therapeutically as antiasthmatic and antiallergenic drugs. Non-therapeutic applications of these active functionalized drugs include receptor probes, immobilized ligands for affinity chromatography, and radiolabeled analogs.

A further benefit of applying the congener approach to xanthines is the opportunity to increase water solubility. The series of super-active 8-phenylxanthines is highly non-polar with aqueous solubility very often falling below 10 micromolar. By increasing water solubility through the attachment of highly polar charged or uncharged groups, it is possible to overcome undesirable binding to plasma proteins and partition into lipids. This leads to improved pharmacokinetics of the drugs.

Some similar known compounds, such as the 8-arylxanthines, contain up to four substituents on the phenyl ring. These substituents usually contribute to the compound's insolubility in water. The present invention not only discloses only one substituent on the phenyl ring, it also discloses a variety of charged and uncharged hydrophilic substituents attached to xanthine through a functionalized chain.

GENERAL DESCRIPTION OF THE INVENTION

The present invention discloses the synthesis of a series of highly potent congeners of theophylline and 1,3-dipropylxanthine. Some of these congeners contain groups designed for radiolabeling through introduction of radioisotopes of elements such as iodine, carbon, fluorine, or through metal complexes. The radioisotope is attached by linking the drug to a "radioisotope acceptor unit," which is specially designed for the facile introduction of a particular isotope. These radiolabeled compounds have high receptor affinities and contain short-lived positron emitters, such as $^{18}$F, and are potentially useful for the developmental diagnostic technique of positron emission tomography. Other functionalized congeners of this invention are suitable for the preparation of affinity columns.

As noted above, the compounds of this invention are characterized by the presence of lower alkyl groups such as n-propyl groups at the 1 and 3 position on the theophylline ring and by a variety of para-substituents on the 8-phenyl ring. It should be noted, however, that some of the compounds of this invention retain the dimethyl groups of theophylline. The compounds of this invention are of the general formula

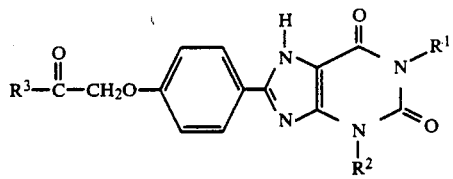

wherein
$R^1$ and $R^2$ = a carbon chain of 1-6 carbons;
$R^3$ = carboxylic acids (OH—), alkoxy, aryloxy, N-oxyimide; or
wherein
$R_3 = R^4R^5N$
  wherein $R^5$ is hydrogen, alkyl, aryl, or alkylaryl groups; and
  wherein $R^4 = R^5$ or $x(CH_2)_nNH$
  wherein $x =$
    primary, secondary, or tertiary amino group; or
    secondary or tertiary amino group wherein one of the amine substituents is a p-hydroxybenzyl group; or
  hydroxy or carboxy; or acyl-amino group of the form R⁶NH;
wherein R⁶=
  lower carboxylic acid, optionally substituted with at least one halogen; or
  alpha-amino acid of the L or D configuration; or
  N-benzyloxycarbonyl alpha-amino acid of the L or D configuration; or
  biotin, optionally bonded through an amide linkage to a straight chain omega-amino acid having between 1 and 6 methylene groups; or
  2-thiopheneacetic acid;
n=1-10
and pharmaceutically acceptable salts.

The compounds of this invention are produced by processes described in the examples.

Utility Statement

Selected compounds of this invention have shown significant activity as antiallergenic and anti-asthmatic drugs by standard pharmacological tests. Theophylline and other xanthine derivatives are used clinically in the treatment of asthma, cardiac or renal failure, high blood pressure, and depression; i.e., conditions involving the inhibition or blocking of adenosine receptors. The present compounds are adenosine antagonists and, as such, are useful in the same manner as theophylline and other xanthine derivatives. Furthermore, the present compounds are more water-soluble and more potent than most known xanthine derivatives. Moderate selectivity depending on the nature of the group attached to the functionalized congener has been demonstrated, thus reducing the side effects associated with the administration of known adenosine receptor antagonists. Table 2 shows the solubility values of these compounds.

Specific Disclosure

The compounds of the present invention are of the general formula:
wherein
$R^1 R^2 = C_1-C_6$ and
$R_3$ is any one of the 8-phenyl substituents illustrated in Table 1.

The preferred compounds of this invention are $R_1 = R_2 = CH_2CH_3$ and $R_3 = H_2N-NHCOCH_2-$, (6g)

$H_2N-(CH_2)_2NHCOCH_2-$, (6d)

$H_2N-(CH_2)_8NHCOCH_2-$, (6e)

(9b)
HO—⟨phenyl⟩—CH₂N(CH₂)₂NHCOCH₂—CH₂CH₃.HOAC, $HO_2C-CH_2$, (1b)

(5)
⟨succinimide⟩N—OCOCH₂—, and

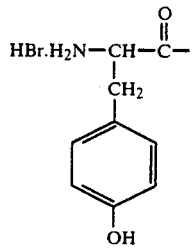
(53)

All of these compounds combine high potency with high solubility. The solubility value is partly due to the covalent attachment of polar groups (i.e., para substituents on the 8-phenyl ring) noted above and is therefore not intended to be limited by the polar groups specifically designated. Examples of the compounds of this invention, as well as their activity and solubility are set out in Table 1.

Polar groups that promote water solubility and are uncharged at physiological pH include carboxamide, ureide, alcohol, amide, ether, carbamate, nitrogen heterocycle, hydrazide, and sulfonamide. Charged polar groups include alkylamino, carboxyl, sulfonate, guanidine, phosphate, metal salts and their complexes.

IC₅₀ values for A₁-receptors were obtained from antagonism of binding of 1 nM [³H]cyclohexyladenosine to rat cerebral cortical membranes. IC₅₀ values for A₂-receptors were obtained from antagonism of [³H]cyclic-AMP accumulation elicited by 15 M 2-chloroadenosine in [³H]adenine-labeled guinea pig cerebral cortical slices. $K_i$ values were calculated from the equation $K_i = IC_{50}/(1 + \text{conc. of adenosine analog}/K_a$ for adenosine analog).

The ratio of A₂ to A₁ indicates the degree of specificity of the particular compound (low values represent high A₂-receptor specificity). The compounds with A₂ specificity are expected to be more useful as anti-allergenic or anti-asthmatic agents. Compounds with high A₁ specificity in general block the cardiac depressant effects of adenosine without diminishing blood flow to the heart, thus they may be more useful therapeutically in treating cardiac insufficiency and angina. Some analogs are expected to have activity as inhibitors of phosphodiesterase, as do theophylline and caffeine, thus contributing anti-allergenic and anti-asthmatic activity. The solubility of these compounds is also shown and should be noted as an index to a compound's medicinal value—a compound that does not dissolve in water cannot be used therapeutically. If the ratio of A₂ to A₁ is low, the compound is A₂-selective and is anti-allergenic or anti-asthmatic (without cardiovascular effects). The ideal ratio is about 0.1, but this has never been achieved. The most selective A₂ antagonists known prior to this invention is about 0.6. Note that preferred compounds 1b and 6g are more selective.

If the ratio of A₁ to A₁ is high, the compound is A₁-selective and exhibits lipolytic and cardiac stimulant properties. Most known compounds of interest are no lower than 10. Note that many of the compounds of this invention are significantly higher than 10.

Synthetic Methods

The carboxylic acid congener of theophylline (1a), its dipropyl analog (1b), and the other 1,3-dialky analogs are synthesized by a standard approach to xanthines, as described in U.S. Pat. No. 4,452,788. Briefly, 5,6-diamino-1,3-dimethyluracil ($R^1=R^2=CH_2$) is commercially available, but other 1,3-dialkyl compounds are prepared with appropriate dialkyl urea and cyanoacetic acid. These reactions are decribed in *J Org. Chem.*, Vol. 16, p. 1879 (1951) and *Can. J. Chem.*, Vol. 46, p. 3413 (1968). The imidazole ring is formed by oxidative closure of the benzylidene adduct derived from the appropriate diaminouracil and a substituted benzaldehyde (13). This compound (Y=COOH) is the product of alkylation of p-hydroxybenzaldehyde by iodoacetate.

Ring closure of the benzylidene adduct occurs by heating with substoichiometric amounts of anhydrous ferric chloride. In the case of the carboxylic acid derivatives, considerable ethyl ester (3) is formed using ethanol as a solvent. To avoid separating the mixture of acid and ethyl ester, the esterification is brought to completion by prolonged heating of the reaction mixture in the presence of one equivalent of ferric chloride. Use of trifluoroethanol as the solvent during ring closure produces 1 exclusively. Compound 1 may alternatively be prepared by basic hydrolysis of the ester (3).

Coupling of the carboxylic acid congeners to amines using carbodiimides presents problems due to limited solubility. Attempts to couple 8b to various polar amines using carbodiimides in dimethylformamide often results in isolation of the N-acylurea (4) derived from the acid and the coupling reagent. Compound 1a is coupled in low yield to p-toluidine. In an alternate approach to amide formation, the N-hydroxysuccinimide ester (5) of the carboxylic acid congener is prepared and is readily separable from the N-acylisourea by crystallization. The N-hydroxysuccinimide esters and the watersoluble esters of N-hydroxy-2-sulfosuccinimide of the carboxylic acid congeners are activated forms of the drug for coupling to amines, including biopolymers such as proteins, to serve as drug carriers. These drug derivatives may also be attached to directed carriers such as monoclonal antibodies.

Alternatively, an amide bond may be introduced on the substituted benzaldehyde (e.g., 15, amide) prior to formation of the imidazole ring.

The ethyl ester (3) may be aminolyzed by excess unhindered amines in dimethylformamide to form amides (6). Aminolysis by alkyl diamines produces the functionalized amino congeners (6d, e), which are the basis for additional derivatives including amides (7 and 8) and secondary and tertiary amines (9), made via reductive amination. See the examples for additional description of these synthesis procedures.

Biological Activity

The 1,3-dialkyl-8-(p-hydroxyphenyl)xanthine, from which the functionalized congeners are formalistically derived, have been shown in earlier studies to be potent antagonists of $A_1$- and $A_2$-adenosine receptors [*PNAS*, Vol. 77, p. 5547 (1980)]. 8-p-Hydroxyphenyltheophylline is 280-fold more potent than theophylline in displacing [$^3H$]cyclohexyladenosine from $A_1$-adenosine receptors in rat cerebral cortical membranes and is 107-fold more potent than theophylline in antagonizing $A_2$-adenosine receptor mediated activation of cyclic AMP-generation by 2-chloroadenosine in guinea pig cerebral cortical slices. Replacement of the 1,3-dimethyl groups with n-propyl groups yields 1,3-dipropyl-8-(p-hydroxyphenyl)xanthine (2b). This analog is an extremely potent $A_1$-adenosine antagonist with a $K_i$ value versus [$^3H$]cyclohexyl-adenosine binding in rat cerebral cortical slices of 2.9 nM. The change in the alkyl residues, thus, has incresed potency at $A_1$-receptors by about 17 fold. The change in alkyl residues also increases potency at $A_2$-receptors but to a much lesser extent (2.6-fold), yielding a somewhat selective $A_1$-antagonist.

Functionalization of these two xanthines is based on the presence of a p-carboxymethyloxy residue on the 8-phenyl ring. This functionalization permitted facile synthesis of a wide variety of amides. In the case of the 8-phenyltheophyllines, the p-carboxymethyloxy compound (1a) has a ten-fold lower activity than the p-hydroxy compound at $A_1$-receptors and a 3.3-fold lower activity at $A_2$-receptors (Table 1). It appears likely that the presence of the anionic carboxyl group is not favorable to high affinity binding to either receptor. With an anionic p-carboxyl group directly on the 8-phenyl ring, even lower activity pertained with $K_i$ values of 3000 nM at $A_1$-receptors and 2500 nM at $A_2$-receptors. A p-toluide function (2a) was well tolerated by both $A_1$ and $A_2$-receptors, and this neutral derivative of a functionalized congener was about 2-fold more potent than 8-(p-hydroxyphenyl)theophylline at $A_1$-receptors and about 6-fold more potent at $A_2$-receptors (Table 1).

Further syntheses of functionalized congeners were based on the anticipation that the higher potency and selectivity of 1,3-dipropyl-8-(p-hydroxyphenyl)-xanthine relative to the 1,3-dimethyl homolog enhances the activity of the p-carboxymethyloxy congeners and derivatives even further. The p-carboxymethyloxy compound (26) is 20-fold less potent than the p-hydroxy compound at $A_1$-receptors. At $A_2$-receptors the p-carboxymethyloxy compound is nearly equipotent with the p-hydroxy compound. Again, it appears likely that the presence of the anionic carboxy group mitigates against high activity at the $A_1$-receptors. Similarly, 8-p-carboxy-1,3-dipropylxanthine is about 60-fold less active than the p-hydroxy compound at $A_1$-receptors, while being only 2-fold less active at $A_2$-receptors nearly identical to that of the anionic carboxylic acid. The carboxamide (6a) is very active at $A_1$-receptors and moderately selective, being 8-fold more active at $A_1$-receptors than at $A_2$-receptors. Remarkably, the p-toluide (2b) is no more potent than the acid at $A_1$ receptors, while being 22-fold less potent than the acid at $A_2$-receptors. This finding stands in direct contrast to results obtained with the analogous compounds in the theophylline (1,3-dimethyl) series, in which series the p-toluide was about 20-fold more active than the acid both at $A_1$-receptors and at $A_2$-receptors. It is believed that contributions to affinity afforded by the 1,3-dialkyl substituents and by para-substituents on the 8-phenyl ring are not independent and can greatly influence each other in either a positive or a negative manner. For example, the p-hydroxyanilide (2c) is nearly 10-fold more potent than the p-toluide at both $A_1$- and $A_2$-receptors, thus illustrating the potential importance of minor structural modifications distant from the primary pharmacophore (in this case the 8-phenylxanthine) on biological activity. The o-hydroxy-m-sulfoanilide (6f) is synthesized as a water-soluble xanthine suitable for radioiodination. It is not selective, and its potency was at least three-fold less than the parent acid.

The aminoethylamide (6d) is synthesized with a view of increasing water solubility and also of providing a key intermediate for preparation of affinity columns, fluorescent probes and a biotin-containing xanthine.

The aminoethylamide is very potent at $A_1$-adenosine receptors with a $K_i$ value of 1.2 nM. It was some forty-fold less potent at $A_2$-adenosine receptors. The presence of a p-hydroxybenzyl and ethyl substituents (9b) (phenol suitable for radioiodination) on the terminal amino group exhibits little effect on the potency at $A_1$-receptors, while reducing potency at $A_2$-receptors by over four-fold. This compound is the most selective $A_1$-antagonist (145-fold) in the present series.

A number of compounds were prepared in which the terminal amino group was acylated. The acetyl compound (14a) is 20-fold less potent than the parent amine at $A_1$-receptors while the biotinyl compound (7d) is 45-fold less potent. Potency at the $A_2$-receptor is not significantly affected in the case of the acetyl compound, while potency for the biotinyl compound is reduced at $A_2$-receptors by only three-fold. Both acyl compounds are, thus, relatively nonselective antagonists for $A_1$-and $A_2$-adenosine receptors in contrast to the parent amine which exhiits a 40-fold selectivity for $A_1$-receptors. The potency of the acetyl compound suggests that affinity columns prepared through acyl coupling to the amino compound could be effective in isolation of solubilized $A_1$- and $A_2$-receptors and/or xanthine-binding sites.

The use of longer spacer chains appears feasible for preparation of affinity columns if the aminoethylamide proves unsatisfactory. The aminooctylamide (6e) was only 5-fold less potent than the aminoethylamide (6d) at $A_1$-receptors and about 2-fold less potent at $A_2$-receptors.

A bulky ureide (4) was found to have relatively low activity at both $A_1$- and $A_2$-receptors.

The compounds of the invention form pharmaceutically acceptable salts with both organic and inorganic acids and bases. Examples of suitable acids for salt formation are hydrochloric, sulfuric, phosphoric, acetic, citric, oxalic, malonic, salicylic, malic, fumaric, succinic, ascorbic, maleic, methansulfonic, and the like. The salts are prepared by contacting the free base form with an equivalent amount of the desired acid in the conventional manner. Examples of suitable bases for salt formation are sodium hydroxide, sodium carbonate, sodium bicarbonate, potassium hydroxide, calcium hydroxide, ammonia, organic amines, and the like. The salts are prepared by contacting the free acid form with an equivalent amount of the desired base in the conventional manner.

In summary, the functionalized congener approach to xanthine antagonists for adenosine receptors has yielded a series of potent compounds which in some cases are moderately selective for $A_1$- or $A_2$-receptors. The effects on biological activities caused by modifications of functions distal from the primary pharmacophore in some cases are quite impressive. Dramatically high potency at the $A_1$-receptor is associated with the presence of an alkyl amino group on the chain attached to the 8-phenyl ring.

Affinities of congeners and derivatives for the $A_1$-receptors seems somewhat more sensitive to distal modifications than affinities for the $A_2$-receptor. As yet no selective $A_2$-receptor antagonists have been discovered and as yet no highly specific $A_1$-receptor antagonists are available. The present set of functionalized xanthines are improved analogs of theophylline and caffeine and will thus have more selective antiasthmatic, diuretic, respiratory stimulant, central stimulant, cardiac stimulant, analgesic adjuvant, and anti-inflammatory applications.

TABLE 1

| Compound | 8-Phenyl Substituent | $K_i$ (nM) $A_1$-Receptor | $K_i$ (nM) $A_2$-Receptor | $A_2/A_1$ Ratio | Name |
|---|---|---|---|---|---|
| 1a* | $HO_2C-CH_2$ | 500 ± 200 | 430 ± 80 | 0.86 | 8-(4'-carboxymethyloxyphenyl)-1,3-dimethyl-xanthine |
| 1b | $HO_2C-CH_2$ | 58 ± 3 | 34 ± 13 | 0.59 | 8-(4'-carboxymethyloxyphenyl)-1,3-dipropyl-xanthine |
| 2a* | 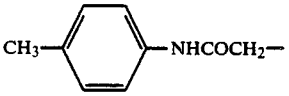 $CH_3$—⟨ ⟩—$NHCOCH_2$— | 26 ± 5 | 20 ± 7 | 0.77 | 8-(4'-carboxymethyloxyphenyl)-1,3-dimethyl-xanthine |
| 2b | $CH_3$—⟨ ⟩—$NHCOCH_2$— | 36 ± 23 | 750 ± 370 | 21.0 | 8-(4'-carboxymethyloxyphenyl)-1,3-dipropyl-xanthine-4-methyl-anilide |
| 2c | HO  $NHCOCH_2$— | 4.1 ± 1.5 | 62 ± 37 | 15.0 | 8-(4'-carboxymethyloxyphenyl)-1,3-dipropyl-xanthine-4-hydroxy-anilide |
| 3 | $CH_3CH_2OCO-CH_2$— | 42 ± 3 | 30 ± 12 | 0.71 | 8-(4'-carboxymethyloxyphenyl)-1,3-dipropyl-xanthine ethyl ester |
| 4 | 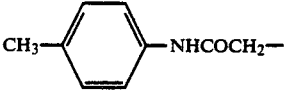 ⟨S⟩—NHCON—$COCH_2$ / ⟨S⟩ | 96 ± 25 | >1000 (30% inhibition) | >10 | N—[8-(4'-carboxymethyloxyphenyl-1,3-dipropyl-xanthine]dicyclohexylurea |

TABLE 1-continued

| Compound | 8-Phenyl Substituent | $K_i$ (nM) A$_1$-Receptor | $K_i$ (nM) A$_2$-Receptor | A$_2$/A$_1$ Ratio | Name |
|---|---|---|---|---|---|
| 5 | (succinimide structure) N—OCOCH$_2$— | 9.0 ± 0.7 | 30 | 3.3 | 8-(4'-carboxymethyloxyphenyl)-1,3-dipropyl-xanthine n-hydroxysuccinimide ester |
| 6a | H$_2$NCOCH$_2$— | 6.0 ± 1.0 | 47 ± 2 | 7.8 | 8-(4'-carboxymethyloxyphenyl)-1,3-dipropyl-xanthine carboxamide |
| 6b | (CH$_3$)$_2$CHNHCOCH$_2$— | | | | 8-(4'-carboxymethyloxyphenyl)-1,3-dipropyl-xanthine isopropylamide |
| 6c | (CH$_3$)$_2$NCOCH$_2$— | 32 ± 7 | 68 ± 39 | 2.1 | 8-(4'-carboxymethyloxyphenyl)-1,3-dipropyl-xanthine dimethylamide |
| 6d | H$_2$N—(CH$_2$)$_2$NHCOCH$_2$— | 1.2 ± 0.5 | 49 ± 17 | 41.0 | 8-(4'-carboxymethyloxyphenyl)-1,3-dipropyl-xanthine aminoethylamide |
| 6e | H$_2$N—(CH$_2$)$_8$NHCOCH$_2$— | 5 | 470 | 94 | 8-(4'-carboxymethyloxyphenyl)-1,3-dipropyl-xanthine aminooctylamide |
| 6f | (sulfoanilide structure with OH, NHCOCH$_2$—, C$_2$H$_5$—NH, O$^-$O$_3$S) | 150 | 150 | 1.0 | 8-(4'-carboxymethyloxyphenyl)-1,3-dipropyl-xanthine-o-hydroxy-m-sulfoanilide |
| 6g | H$_2$N—NHCOCH$_2$— | 59 ± 0.7 | 32 | 0.54 | 8-(4'-carboxymethyloxyphenyl)-1,3-dipropyl-xanthine hydrazide |
| 7a | CH$_3$CONH—(CH$_2$)$_2$—NHCOCH$_2$— | 24 ± 3.5 | 62 ± 3 | 2.6 | 8-(4'-carboxymethyloxyphenyl)-1,3-dipropyl-xanthine 2-(acetylamino)-ethylamide |
| 7b | BrCH$_2$CONH(CH$_2$)$_2$NHCOCH$_2$— | 33 | | | 8-(4'-carboxymethyloxyphenyl)-1,3-dipropyl-xanthine 2-(bromoacetylamino)-ethylamide |
| 7c | (thienyl)CH$_2$CONH—(CH$_2$)$_2$—NHCOCH$_2$ | 9 | | | 8-(4'-carboxymethyloxyphenyl)-1,3-dipropyl-xanthine 2-(2'-thienylacetylamino)-ethylamide |
| 7d | (biotinyl)(CH$_2$)$_4$CONH(CH$_2$)$_2$—NHCOCH$_2$— | 54 ± 2 | 180 ± 80 | 3.3 | 8-(4'-carboxymethyloxyphenyl)-1,3-dipropyl-xanthine 2-(biotinylamino)-ethylamide |
| 7e | (biotinyl)(CH$_2$)$_4$CONH(CH$_2$)$_5$CO—NHCOCH$_2$— | 52 | | | 8-(4'-carboxymethyloxyphenyl)-1,3-dipropyl-xanthine 2-(biotinylaminocapropylamino)-ethylamide |

TABLE 1-continued

| Compound | 8-Phenyl Substituent | $K_i$ (nM) A₁-Receptor | $K_i$ (nM) A₂-Receptor | A₂/A₁ Ratio | Name |
|---|---|---|---|---|---|
| 8a | HBr·H₂N—CH(CH₂-C₆H₄-OH)—C(O)—Z | 2.9 | | | 8-(4'-carboxymethyloxyphenyl)-1,3-dipropyl-xanthine 2-(L-tyrosinylamino)-ethylamide |
| 8b | C₆H₅—CH₂—O—C(O)—NH—CH(CH₂-C₆H₄-OH)—C(O)—Z | 23 | | | 8-(4'-carboxymethyloxyphenyl)-1,3-dipropyl-xanthine 2-(N—benzyloxycarbonyl)-L-tyrosylamino)-ethylamide |
| 9a | HO—C₆H₄—CH₂—Z | not tested | | | 8-(4'-carboxymethyloxyphenyl)-1,3-dipropyl-xanthine-2(N—(4-hydroxy)benzylaminoethylamide |
| 9b | HO—C₆H₄—CH₂N(CH₂CH₃·HOAc)(CH₂)₂NHCOCH₂— | 2.2 + 0.7 | 320 + 70 | 145 | 8-(4'-carboxymethyloxyphenyl)-1,3-dipropyl-xanthine-2(N—4-hydroxybenzyl-methylamino)-ethylamide acetate |
| 9c | OH—C₆H₃(F)—CH₂—NH—(CH₂)₂—NHCOCH₂ | Not tested | | | 8-(4'-carboxymethyloxyphenyl)-1,3-dipropyl-xanthine-2(N—(3-fluoro-4-hydroxy)benzylamino)-ethylamide |
| 10 | HOOC—(CH₂)₄—CH(CH₃)—Z | Not tested | | | 6-[N—(8-(4'-carboxymethyloxyphenyl)-1,3-dipropyl-xanthine-2-ethylamide]-n-heptanoic acid |

*1,3-Dimethylxanthine; all others are 1,3-dipropyl- $$Z = -NH-(CH_2)_2-NH-\overset{O}{\overset{\|}{C}}-CH_2-O-$$

the 8-phenyl substituent is attached to

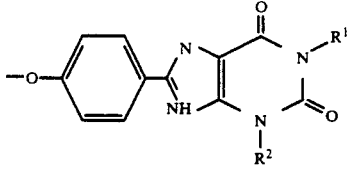

TABLE 2

| Compound | 8-Phenyl Substituent | Solubility* |
|---|---|---|
| — | HO— | 3.2 micromolars |
| 1b | HO₂C—CH₂—O— | 1.2 millimolars |
| 6a | H₂NCOCH₂—O— | 26 micromolars |
| 6d | H₂N—(CH₂)₂NHCOCH₂—O— | 90 micromolars (primary amine with 2 methylenes) |
| 6g | H₂N—NHCOCH₂—O— | 36 micromolars |
| 7a | CH₃CONH—(CH₂)₂—NHCOCH₂—O— | 8.6 micromolars |

TABLE 2-continued

| Compound | 8-Phenyl Substituent | Solubility* |
|---|---|---|
| 8b | $H_2N-CH-CONH-(CH_2)_2-$ <br> $\quad\quad\quad\mid$ <br> $\quad\quad\quad CH_2$ <br> [para-hydroxyphenyl] <br> $\quad\quad\quad NHCOCH_2-O-$ | 36 micromolars |
| 10 | $\quad\quad CH_3$ <br> $\quad\quad\quad\mid$ <br> $HOOC-(CH_2)_4CH-NH-$ <br> $(CH_2)_2NHCOCH_2-O-$ | 110 micromolars |

*pH 7.2, 0.1 M sodium phosphate
A value of 20 for solubility is deemed superior with reference to this table.

EXAMPLES

In all of the following examples, thin layer chromatography (TLC) was carried out using Analtech silica gel GF plates using mixtures of chloroform/methanol/acetic acid (v/v; A: 50/50/5; B: 94/4/2). Reagent grade dimethylformamide (DMF, Aldrich gold label) was stored over 3Å molecular sieves. Proton NMR spectra were taken on a Varian 220 MHz instrument in the Fourier transform mode. Dicyclohexylcarbodiimide (DCC) was purchased from Sigma. 5,6-Diaminouracil hydrate in Example 3 was purchased from Aldrich.

EXAMPLE 1

4-(Carboxymethyloxy)benzaldehyde (A)

To a solution of p-hydroxybenzaldehyde (49 g, 0.40 mol) were added iodoacetic acid (75 g, 0.40 mol) and potassium carbonate (anhydrous, 120 g), and the magnetically stirred mixture was warmed at 60° C. for three days. The resulting solid was dispersed mechanically in a mixture of ethyl acetate (400 ml) and water. The mixture was neutralized cautiously with phosphoric acid. After the dissolution of the solid mass, the neutral aqueous layer was withdrawn. The organic layer was extracted repeatedly with a concentrated solution of dibasic sodium phosphate, to remove additional acidic organic material. The aqueous extracts were combined, filtered through glass wool, and acidified to pH 1 using 6N HCl. This solution was placed in the refrigerator overnight, and a product of tan crystals (21.85 g) was collected. Unreacted p-hydroxybenzaldehyde was recovered upon evaporation of the organic layer. Yield based on recovery of starting material was 60%. Mp 191°–193° C. Analysis ($C_9H_8O_4$): calc. 60.00% C, 4.48% H; found 59.66% C, 4.37% H.

4-(Carboxymethyloxy)benzaldehyde p-toluide

Dicyclohexylcarbodiimide (DCC, 1.32 g, 6.4 mmol) was added to a solution of compound A (1.15 g, 6.4 mmol) in tetrahydrofuran (50 ml). After stirring for ten minutes p-toluidine (0.7 g, 6.5 mmol) was added. After one hour, the precipitate was removed by filtration, and the filtrate was reduced in volume by evaporation. A crystalline product (1.09 g, 63% yield) was obtained by trituration of the filtrate with petroleum ether. An analytical sample was obtained by thin layer purification (solvent B) which was necessary for the removal of a faster moving impurity, later shown by C,H,N analysis to be the imine adduct of the product with p-toluidine.

4-(Carboxymethyloxy)benzaldehyde p-hydroxyanilide

Compound A (1.80 g, 10 mmol) was dissolved in 25 ml of tetrahydrofuran containing 20% DMF. To this solution were added DCC (2.06 g, 10 mmol) and after ten minutes a solution of p-aminophenol hydrochloride (1.46 g, 10 mmol) and triethylamine (0.78 g, 10 mmol) in DMF (10 ml). After 2 hours the precipitate was removed by filtration and washed with tetrahydrofuran. The combined filtrates were evaporated and triturated with water. A yellow oil separated and crystallized, providing 2.40 g (89%) of product. The product was recrystallized from ethanol/petroleum ether to give a white solid which melted at 185°–186° C. Analysis ($C_{15}H_{13}NO_4$): calc. 66.41% C, 4.83% H, 5.16% N; found 66.11% C, 5.07% H, 5.36% N.

EXAMPLE 2

6-Amino-1,3-dipropyl-5-(4'-carboxymethyloxybenzylideneamino)uracil

A representative synthesis of benzylidene adduct is given. Compound A (1.51 g, 8.37 mmol) was dissolved in a mixture of methanol (35 ml) and acetic acid (5 ml) in a 50 ml boiling flask on a steam bath. To this was added a methanolic solution (60 ml) of freshly synthesized 5,6-diamino-1,3-dipropyluracil. After heating 15 minutes, the volume was reduced by evaporation until crystallization occurred. Ether (40 ml) was added and the nearly white solid was collected. Yield 2.80 g (86%), mp 179°–180° C. Analysis ($C_{19}H_{24}N_4O_5$): calc. 58.60% C, 6.21% H, 14.39% N; found 58.72% C, 6.16% H, 14.43% N.

EXAMPLE 3

8-(4'-Carboxymethyloxyphenyl)-1,3-dimethylxanthine (1a)

The benzylidene adduct was prepared as described in Example 2 from compound A (0.609 g, 3.38 mmol) and 5,6-diamino-1,3-dimethyluracil hydrate (0.58 g, 3.4 mmol). Tan crystals (0.963 g, 85.7%) were obtained upon cooling the reaction mixture overnight in the refrigerator. The benzylidene adduct (98 mg), used without further purification, was dissolved in warm DMF (7 ml), treated with ferric oxide (20 mg) and heated on the steam bath for four hours. After adding an equal volume of ethanol, the precipitate was collected and dried. Yield 76 mg (67% overall yield), not melting up to 310° C.

EXAMPLE 4

8-(4'-Carboxymethyloxyphenyl)-1,3-dipropylxanthine (1b)

Method A: The benzylidene adduct (191 mg, 0.49 mmol) was suspended in trifluoroethanol (15 ml) and dissolved by refluxing on a steam bath. Anhydrous ferric chloride (20 mg) was added and heating was continued for two hours. Ether was added to complete the precipitation of product, which was collected and dried in vacuo. The crude product, 0.17 g (89%), was recrystallized from DMF/methanol/ether to give analytically pure material, mp 283°–285° C. Analysis ($C_{19}H_{22}N_4O_5$): calc. 59.06% C, 5.74% H, 14.50% N; found 59.03% C, 5.33% H, 14.24% N.

Method B: The ethyl ester (114 mg, 0.28 mmol) was dissolved in DMF (5 ml) and treated with sodium carbonate (5 ml, 0.1N). The mixture was heated on the steam bath for one-half hour. The solvent was evaporated, leaving a white film, which was triturated with dilute HCl. The resulting white precipitate was collected and washed with water and dried in vacuo. This material was homogeneous by TLC (solvent B; $R_f$ 0.42) and identical to the product prepared by method A. Yield 105 mg (99%).

EXAMPLE 5

8-(4'-Carboxymethyloxyphenyl)-1,3-dipropyl xanthine 4-methylanilide (2b)

The p-toluide of the carboxylic acid congener (1b) was prepared by the method described below for compound 2c, except that the reaction was continued overnight.

8-(4'-Carboxymethyloxyphenyl)-1,3-dipropyl xanthine 4-hydroxyanilide (2c)

The benzylidene adduct formed from freshly prepared 5,6-diamino-1,3-dipropyluracil (see Example 2) (0.385 mmol) and the substituted benzaldehyde (88 mg, 0.325 mmol) was formed according to the method described for the compound in Example 2. The solid adduct (0.14 g, 90% yield) was dissolved in hot absolute ethanol (10 ml), treated with ferric chloride (20 mg) and heated on the steam bath until the product precipitated (30 min). Ether was added and the product (93 mg, 60% overall yield from 5,6-diamino-1,3-dipropyluracil and 4-(carboxymethyloxy)benzaldehyde) was isolated.

EXAMPLE 6

8-(4'-Carboxymethyloxyphenyl)-1,3-dipropylxanthine ethyl ester (3)

The compound from Example 2 (1.69 g, 4.3 mmol) was suspended in 100 ml absolute ethanol. Anhydrous ferric chloride (0.70 g, 4.3 mmol) was added, and the mixture was refluxed on a steam bath for one day. The slow conversion of the free acid (identical to compound 1b, $R_f$ 0.35) to the ethyl ester ($R_f$ 0.78) was followed by TLC on silica gel using solvent B. The reaction mixture was evaporated in vacuo to a small volume, and dry ether was added. The bulky crystalline mass was collected by filtration, washed with ether, and dried in vacuo. Yield 1.27 g (70.8%), mp 243°–244° C. Analysis ($C_{21}H_{26}N_4O_5$): calc. 60.86% C, 6.23% H, 13.51% N; found 60.42% C, 5.80% H, 13.50% N.

EXAMPLE 7

8-(4'-Carboxymethyloxyphenyl)-1,3-dipropylxanthine N-hydroxysuccinimide ester (5)

The carboxylic acid congener (compound 1b, 18.4 mg, 0.048 mmol) was dissolved in DMF (5 ml), cooled in an ice bath, and treated with N-hydroxysuccinimide (6 mg) and DCC (11 mg). After stirring for one day at room temperature, the urea was removed by filtration. Upon addition of water, a white solid precipitated and was collected. Recrystallization from DMF/water provided 11.1 mg of the pure product (48% yield). A side product removed by crystallization was identical to the N-acyl urea.

EXAMPLE 8

8-(4'-Carboxymethyloxyphenyl)-1,3-dipropyl xanthine 2-aminoethylamide (6d)

Compound 3 (57.5 mg, 0.14 mmol) was dissolved in warm dimethylformamide (1.0 ml). Upon reaching room temperature ethylene diamine (1.0 ml) was added. After stirring overnight most of the solvent was evaporated under a stream of nitrogen. The resulting oil was triturated with methanol. After crystallization began, ether was added and the product was collected and dried. Yield 59 mg (99%), melting at 214°–216° C. with decomposition, homogeneous by TLC (solvent system A).

EXAMPLE 9

8-(4'-Carboxymethyloxyphenyl)-1,3-dipropylxanthine 2-(biotinylamino)ethylamide (7d)

Compound 6d (24.1 mg, 0.056 mmol) was suspended in 1 ml DMF. N-Hydroxysuccinimido-d-biotin (Sigma, 23.6 mg, 0.069 mmol) was added with stirring. A solution formed after several minutes, and a precipitate appeared soon thereafter. After one day methanol (1 ml) and ether were added. The precipitate was collected and dried (yield 26.6 mg, 73%).

EXAMPLE 10

(A)

8-(4'-Carboxymethyloxyphenyl)-1,3-dipropylxanthine 2-(N-4'-hydroxybenzyl-N-ethylamino)ethylamide acetate (9b)

Compound 6c (56 mg, 0.13 mmol) and 4-hydroxybenzaldehyde (19 mg, 0.16 mmol) were dissolved in warm acetic acid (5%) in ethanol (2 ml) and heated on a steam bath for two hours. The solvent was evaporated and the residue triturated with ether to give 9b, a tan solid (75% yield). NMR (ppm, DMSO, $d_6$): 8.15 (s,1H,CH=N), 8.05 and 7.04 (each d,2H,8-phenyl,J-8.9 Hz), 7.55 and 6.78 (each d,2H,phenol, J=8.5 Hz), 4.56 (s,2H,$CH_2O$), 3.59 ($CH_2N$), 1.91 (s,3H,acetate), and signals from propyl groups. Analysis ($C_{30}H_{36}N_6O_7$) calc: 60.80% C, 6.12% H, 14.18% N; found: 60.93% C, 5.95% H, 14.12% N.

(B)

8-(4'-Carboxymethyloxyphenyl)-1,3-dipropylxanthine 2-(N-4'-hydroxybenzyl-N-ethylamino)ethylamide acetate (9b)

Compound 9b (8.7 mg, 0.015 mmol) was suspended in methanol (1 ml) and treated with excess sodium cyanoborohydride (20 mg, 0.32 mmol). The mixture was warmed at 60° C. to form a solution and treated with acetaldehyde (0.03 ml). After two hours the solvent was evaporated and the residue was chromatographed on LH-20 eluting with methanol. Evaporation of the solvent left a clear film of 16 (5.9 mg, 61%). The product was chromatographically pure ($R_f$ 0.45, Analtech RPS-F, 75% MeOH/5% HOAc/$H_2O$, positive Pauly reaction, unreactive towards ninhydrin). An average molecular weight of 563 was determined by californium plasma desorption mass spectroscopy.

EXAMPLE 11

Biochemical assays

Inhibition of binding of 1 nM [$^3$H]$N^6$-cyclohexyladenosine to $A_1$-adenosine receptors in rat cerebral cortical membranes was assayed as described in Daly et al, *Coll. Mol. Neurobiol.*, Vol. 3, p. 6 (1983). Inhibition of binding by a range of concentrations of each xanthine was assessed in triplicate for at least two separate experiments. Inhibition of 2-chloroadenosine-stimulated cyclic AMP accumulation in [$^3$H]adenine-labeled guinea pig cerebral cortical slices was assayed essentially as described in the Daly et al article, supra. In the present experiments 10 μg/ml of adenosine deaminase was present in incubations with slices to prevent effects of endogenous adenosine, and 30 μM 4-(3-cyclopentyloxy-4-methoxyphenyl)-2-pyrrolidone (rolipram, ZK 62711) was present to inhibit phosphodiesterases. Under these conditions 2-chloroadenosine elicited a maximal 10–20 fold increase in levels of radioactive cyclic AMP in guinea pig cortical slices with an EC$_{50}$ of about 8 μM. Inhibition of the response to 15 μM 2-chloroadenosine by a range of concentrations of each xanthine was assessed in triplicate in at least two separate experiments.

EXAMPLE 12

The following are also representative of the claimed invention and may be synthesized in generally the same manner as shown in the preceeding examples.

| | |
|---|---|
| Histamine derivative (can be iodinated) | 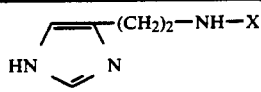 |
| 4° Amine (always + charged) | 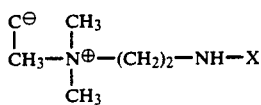 |
| Glassamine (charged and water soluble) | 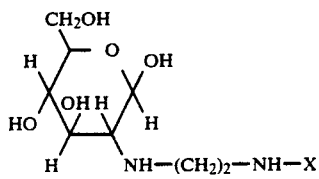 |
| Aminopyridine (charged, H$_2$O soluble and can be iodinated) | 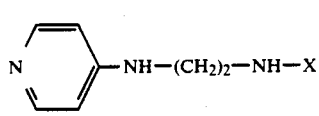 |
| Derivative of diethylenetriamine pentaceticacid (chelator for radioactive metals) | 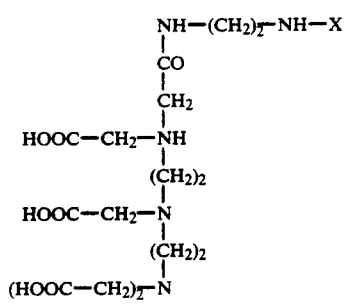 |

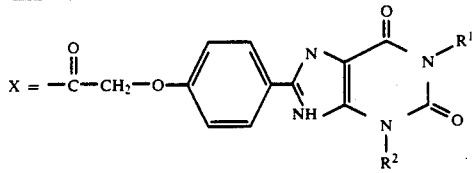

We claim:

1. Compounds having the structural formula

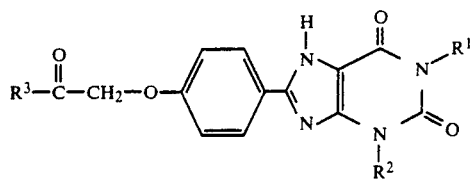

wherein
R$^1$ and R$^2$=an alkyl of 1–6 carbon atoms;
R$^3$=hydroxy, alkoxy of 1 to 4 carbon atoms, phenoxy, N-succinimide; or wherein
R$_3$=R$^4$R$^5$N
wherein
R$^5$ is hydrogen, alkyl of 1 to 4 carbon atoms, phenyl or alkylaryl groups wherein the alkyl has 1 to 4 carbon atoms and the aryl is phenyl; and
wherein R$^4$=R$^5$ or x(CH$_2$)$_n$NH
wherein x=primary, secondary or tertiary amino group wherein the substituents are hydrogen, alkyl having 1–6 carbon atoms or alkylaryl wherein the alkyl contains 1–6 carbon atoms and the aryl is phenyl; or secondary or tertiary amino group wherein one of the amine substituents is a p-hydroxybenzyl group or hydroxy or carboxy or acyl-amino group of the form R$^6$NH and the other is lower alkyl;
wherein R$^6$=a carboxyalkyl group having 1–6 carbon atoms optionally substituted with at least one halogen; or
naturally occurring alpha-amino acids of the L configuration or their D configuration isomers or
N-benzyloxycarbonyl alpha-amino acid of the L or D configuration; or
biotin, bonded through the amide linkage directly or through an amide linkage to a naturally occurring alpha-amino acid having between 2 and 6 carbon atoms or 2-thiopheneacetic acid through the carboxyl group thereof;
n=1–10
and pharmaceutically acceptable salts.

2. The compound of claim 1 having the name 8-(4'-carboxymethyloxyphenyl)-1,3-dipropylxanthine hydrazide.

3. The compound of claim 1 having the name 8-(4'-carboxymethyloxyphenyl)-1,3-dipropylxanthine aminoethylamide.

4. The compound of claim 1 having the name 8-(4'-carboxymethyloxyphenyl)-1,3-dipropylxanthine 2-(N4'-hydroxybenzylmethylamino)ethylamide acetate.

5. The compound of claim 1 having the name 8-(4'-carboxymethyloxyphenyl)-1,3-dipropylxanthine n-hydroxysuccinimide ester.

6. The compound of claim 1 having the name 8-(4'-carboxymethyloxyphenyl)-1,3-dipropylxanthine 2-(L-tyrosinylamino)-ethylamide.

7. The compound of claim 1 having the name 8-(4'-carboxymethyloxyphenyl)-1,3-dipropylxanthine aminooctylamide.

8. A pharmaceutical composition useful as anti-allergy and anti-asthma reagents comprising a compound as defined in claim 1 and the pharmaceutically acceptable salts thereof in combination with the pharmaceutically acceptable carrier.

* * * * *